United States Patent [19]

Strehlke et al.

[11] 4,006,241
[45] Feb. 1, 1977

[54] CERTAIN HALOTHIEN-2-YL 5-NITROTHIAZOL-2-YL KETONES AND FUNGICIDAL COMPOSITION

[75] Inventors: Peter Strehlke; Eberhard Schroeder; Hans-Joachim Kessler, all of Berlin, Germany

[73] Assignee: Schering Aktiengesellschaft, Berlin & Bergkamen, Germany

[22] Filed: July 17, 1974

[21] Appl. No.: 489,161

Related U.S. Application Data

[63] Continuation-in-part of Ser. No. 265,462, June 23, 1972, Pat. No. 3,830,826.

[30] Foreign Application Priority Data

July 18, 1973 Germany .......................... 2337153

[52] U.S. Cl. ........................... 424/270; 260/302 R
[51] Int. Cl.² ...................................... C07D 417/00
[58] Field of Search ................ 260/302 R; 424/270

[56] References Cited

UNITED STATES PATENTS 3,830,826 8/1974 Strehlke et al. ............... 260/302 R

FOREIGN PATENTS OR APPLICATIONS 2,204,364 8/1973 Germany ...................... 260/302 R

OTHER PUBLICATIONS

Horsfall, Fungicides and Their Action, Chronica Botanica, Waltham, Mass., 1945, pp. 150–152.

*Primary Examiner*—R. Gallagher
*Attorney, Agent, or Firm*—Millen & White

[57] ABSTRACT

2-acyl-5-nitrothiazoles of the formula

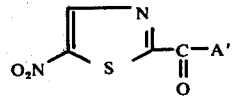

wherein A' is furyl, thienyl or pyrrolyl substituted by halo, or phenyl substituted by 3 to 5 of halo, hydroxy, alkyl or alkoxy of 1–4 carbon atoms, possess antifungal activity, e.g., against *Candida albicans*, *Trichophyton metagrophytes* and *Trichophyton rubrum*.

5 Claims, No Drawings

CERTAIN HALOTHIEN-2-YL 5-NITROTHIAZOL-2-YL KETONES AND FUNGICIDAL COMPOSITION

This is a continuation-in-part of application Ser. No. 265,462, filed June 23, 1972, now U.S. Pat. No. 3,830,826, whose disclosure is incorporated by reference.

BACKGROUND OF THE INVENTION

This invention relates to novel 2-acyl-5-nitrothiazoles.

In U.S. Pat. No. 3,830,826, there are disclosed and claimed compounds of general Formula I

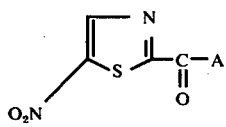

wherein A is a furan, a thiophene, or a pyrrole group, which groups can be substituted by one or more alkyl of 1–7 carbon atoms or by a phenyl group, or is a group of the general Formula II

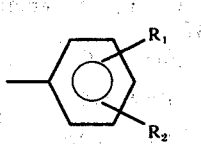

wherein $R_1$ is a hydrogen or halogen atom, alkyl of 1–7 carbon atoms in a straight or branched chain, hydroxy or alkoxy of 1–7 carbon atoms, phenoxy, alkylmercapto of 1–7 carbon atoms, a phenylmercapto, phenyl or phenylalkyl, and $R_2$ is a hydrogen or or halogen atom, alkyl of 1–7 carbon atoms in a straight or branched chain, a hydroxy or alkoxy of 1–7 carbon atoms.

These compounds exhibit a pronounced antifungal activity, especially against Candida albicans and dermatophytes, e.g., Trichophyton mentagrophytes and Trichophyton rubrum. Moreover, the compounds of general Formula I also have a strong effectiveness against bacteria and are valuable intermediates for the preparation of other pharmaceuticals.

It has now been discovered that compounds of general Formula I wherein A is as defined herein also show the above-recited pharmacological effects.

SUMMARY OF THE INVENTION

The novel compounds of this invention are compounds of general Formula III

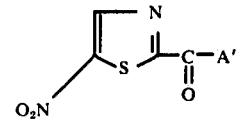

wherein A' is furyl, thienyl or pyrrolyl, each substituted by a halogen atom or is phenyl substituted by 3 to 5 of halogen atom, hydroxy, alkyl of 1–4 carbon atoms or alkoxy of 1–4 carbon atoms.

DETAILED DISCUSSION

Preferred compounds of this invention are those wherein a. A' is halothienyl, preferably 5-halo-2-thienyl, especially wherein halo is bromo or iodo;

b. A' is substituted phenyl wherein one ring substituent is alkoxy of 1–4 carbon atoms, preferebly methoxy, hydroxy or halo, preferably fluoro, and the others are methyl.

The novel compounds can be prepared analogously to the processes described in Ser. No. 265,462, viz., by a. reacting a compound of the general formula A'-H, wherein A' has the above values given with a reactive derivative of 5-nitrothiazole-2-carboxylic acid, in the presence of a Friedel-Crafts catalyst; and b. to prepare the compounds of general Formula III wherein A' is a phenyl group at least one of whose substituents is a hydroxy group, reacting a di-, tri-, or tetrasubstituted phenol with a reactive derivative of 5-nitrothiazole-2-carboxylic acid to obtain the phenol ester, and rearranging the latter in the presence of a Friedel-Crafts catalyst.

As examples of the effectiveness of the compounds of general Formula III against fungi, Table I indicates the minimum inhibitory concentrations (MIC) of several compounds. The comparison compounds are the known 2-Dimethylamino-6-(β-diethylaminoethoxy)-benzothiazole dihydrochloride and two 5-nitrothiazole derivatives substituted in the 2-position, which are known in the literature (J. Med. Chem. 12 [1969] 303).

TABLE 1

| A' | MIC [μg/ml] Against | | |
|---|---|---|---|
| | Cand. alb. | Trich. ment. | Trich. rubr. |
| (CH₃, OH, CH₃, CH₃ phenyl) | 1.6 | 6.3 | 3.1 |
| (F, CH₃, CH₃ phenyl) | 1.6 | 3.1 | 3.1 |

TABLE 1-continued

| A' | MIC [μg/ml] Against | | |
|---|---|---|---|
| | Cand. alb. | Trich. ment. | Trich. rubr. |
| 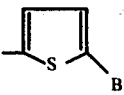 | 0.4 | 1.6 | 1.6 |
| Comparison Compound: | | | |
| 2-Dimethylamino-6-(β-diethylaminoethoxy)-benzothiazole dihydrochloride | 300 | 50 | 50 |
| 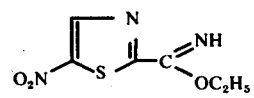 | 50 | 50 | 50 |
| 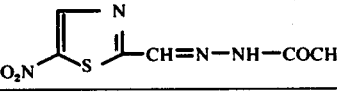 | 25 | 12.5 | 12.5 |

In addition to the compounds of the examples hereinafter other illustrative compounds of this invention which can be produced by the process described herein are e.g. 2-(3-Bromo-2-furoyl)-5-nitrothiazole, 2-(5-tert. butyl-3-chloro-2-methyl-benzoyl)-5-nitrothiazole and 2-(4-butoxy-5-chloro-2-methyl-benzoyl)-5-nitrothiazole.

On the basis of their antifungal spectrum of effectiveness, the novel compounds can be utilized as fungicides in the human and veterinary medicine. They can be utilized, for example, for the topical therapy of mycoses. For therapeutical use, the active agents can be converted into the customary forms of applications, such as, for example, into solutions, powders, creams, sprays, ointments, etc., with the additives usually employed in galenic pharmacy. The concentration of effective agent in the preparations adapted for topical application is about 0.1 – 10%.

For a further discussion of methods suitable for using the compounds of this invention, see Ser. No. 265,462.

Without further elaboration, it is believed that one skilled in the art can, using the preceding description, utilize the present invention to its fullest extent. The following preferred specific embodiments, are, therefore, to be construed as merely illustrative, and not limitative of the remainder of the disclosure in any way whatsoever.

EXAMPLE 1

2-(4-Methoxy-2,3,6-trimethylbenzoyl)-5-nitrothiazole

One gram of 5-nitrothiazole-2-carboxylic acid chloride in 10 ml. of methylene chloride is combined with 850 mg. of 2,3,5-trimethylanisole and then with 1.6 g. of aluminum chloride. After three hours of agitation at room temperature, the reaction mixture is poured on 50 ml. of 1N HCl and extracted with ethyl acetate. After drying of the solution and evaporating the solvent under vacuum, the crystalline residue is recrystallized from methanol/chloroform.

Yield: 30%; m.p. 125°–126° C.

EXAMPLE 2

2-(4-Hydroxy-3,5-dimethylbenzoyl)-5-nitrothiazole

Analogously to Example 1, 5-nitrothiazole-2-carboxylic acid chloride and 2,6-dimethylphenol are reacted with each other.

Yield: 48%; m.p. 203° C. (ethanol/chloroform).

EXAMPLE 3

2-(4-Hydroxy-2,3,5-trimethylbenzoyl)-5-nitrothiazole

Analogously to Example 1, 5-nitrothiazole-2-carboxylic acid chloride and 2,3,6-trimethylphenol are reacted with each other.

Yield: 20%; m.p. 144°–145° C. (ether).

EXAMPLE 4

2-(2-Fluoro-3,4-dimethylbenzoyl)-5-nitrothiazole

Analogously to Example 1, 5-nitrothiazole-2-carboxylic acid chloride and 1-fluoro-2,3-dimethylbenzene are reacted with each other.

Yield: 60%; m.p. 139°–141° C. (methanol/chloroform).

EXAMPLE 5

2-(5-Iodo-2-thenoyl)-5-nitrothiazole

One gram of 5-nitrothiazole-2-carboxylic acid chloride in 10 ml. of methylene chloride is combined with 1.2 g. of 2-iodothiophene and 1 g. of titanium tetrachloride in 5 ml. of methylene chloride. After 2.5 hours of agitation, the mixture is worked up as set forth in Example 1.

Yield: 12%; m.p. 209°–210° C. (methanol/chloroform).

EXAMPLE 6

2-(5-Bromo-2-thenoyl)-5-nitrothiazole

Analogously to Example 5, 1 g. of 5-nitrothiazole-2-carboxylic acid chloride is reacted with 950 mg. of 2-bromothiophene.

Yield: 15%; m.p. 167°–169° C. (methanol/chloroform).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-acyl-5-nitrothiazole of the formula

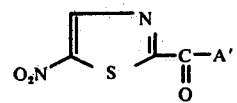

wherein A' is thienyl substituted by bromo or iodo.

2. A compound of claim 1 wherein A' is 5-halo-2-thienyl.

3. A compound of claim 1, 2-(5-iodo-2-thenoyl)-5-nitrothiazole.

4. A compound of claim 1, 2-(5-bromo-2-thenoyl)-5-nitrothiazole.

5. A pharmaceutical composition adapted or topical application comprising an antifungally effective concentration from about 0.1 – 10% of a compound of claim 1 in admixture with a pharmaceutically acceptable carrier.

* * * * *